United States Patent [19]

Madlener

[11] 4,215,985
[45] Aug. 5, 1980

[54] MIXING CONTAINER

[75] Inventor: Bruno Madlener, A-Feldkirch-Tosters, Austria

[73] Assignee: Establissement Dentaire Ivoclar, Schaan, Liechtenstein

[21] Appl. No.: 941,866

[22] Filed: Sep. 13, 1978

[30] Foreign Application Priority Data

Sep. 13, 1977 [DE] Fed. Rep. of Germany ....... 2741184

[51] Int. Cl.² ................................................ A61C 5/04
[52] U.S. Cl. ................................................ 433/90
[58] Field of Search ............... 128/239, 218 M, 272, 128/DIG. 28; 206/219; 222/527; 32/60, 40 A

[56] References Cited

U.S. PATENT DOCUMENTS 1,188,417  6/1916  Dalbey ................................. 32/60
2,648,906  8/1953  Holmes ................................. 32/60
3,655,035  4/1972  Muhlbauer ................... 128/DIG. 28

Primary Examiner—Robert Peshock
Attorney, Agent, or Firm—Becker & Becker, Inc.

[57] ABSTRACT

A container construction for receiving substances adapted to combine with each other for producing viscous medical and dental medical preparations, especially amalgams, which includes: a chamber for receiving a flowable substance which after elimination of a separating wall element is adapted to be conveyed into a mixing chamber preferably containing a pulverous substance. From this mixing chamber the mixed preparation can be pressed out, e.g. by means of a piston. The mixing chamber is at least within the region of its discharging end formed by a bendable discharging tube which is surrounded by a rigid protective sleeve.

17 Claims, 2 Drawing Figures

MIXING CONTAINER

The present invention relates to a container for receiving substances adapted to combine with each other and to produce viscous medical and dental medical preparations. Such preparations include in the medical sector, for instance bone cements and in the dental medical sector, for instance amalgams, dental filling compositions and dental cements which have in common that immediately after the mixing of the substances reacting with each other, they form a viscous mass which eventually hardens. The following description relates primarily to silver amalgam which in the conserving dental art is presently still widely used for fillings, especially in the pre-molar and molar region, even though the mercury required for producing such silver amalgam is highly toxic in the form of its vapors.

Therefore, already mixing containers have been developed for receiving substances reacting with each other and adapted for the manufacture of dental preparations ready for use, which in a mixing chamber contain a preferably pulverous substance for instance silver and a second separate chamber containing a flowable substance, for instance mercury. The flowable substance was brought into the mixing chamber by destroying the partition, and the two substances were thoroughly mixed with each other in said mixing chamber. The finishing mixture was then by means of a piston pressed out of the mixing chamber and was directly applied to the desired area. Such mixing container is described for instance in German Auslegeschrift No. 19,39,316, and a further development of said last mentioned mixing container has been described in German Auslegeschrift No. 24,70,970. With these mixing containers, the mixing chamber has a nozzle-shaped extension which facilitates the application of the mixture at the desired area, for instance a tooth cavity. This nozzle-shaped extension thus acts so-to-speak as delivery tube.

When attempting to bend these delivery tubes in order to better reach the cavities in the molar and premolar region, it sometimes occurred that when pressing out the viscous dental preparation even if it was very thoroughly mixed, inexplainable variations occurred in the composition of said dental preparation, which variations were particularly noticeable with amalgams but also occurred with mixtures of liquid polymerizable monomeres and inorganic filling substances or fillers containing small particles.

The above mentioned separation phenomena manifested themselves in that the proportion of the liquid component at the exit end was first higher than it corresponded to the predosed ratio between liquid and solid components. The reason for this is still not precisely known. It may be assumed that when pressing out the respective preparation, a portion of the liquid component is driven past the stationary solid particles and shortly after the starting of the pressing-out becomes concentrated at the orifice. Probably, the solid particles therefore adhere to the tube walls, while when bending the delivery tube its inner cross sectional surface is reduced. Therefore, for pressing out the mixture, also a greater force is necessary. An amalgam or another dental preparation with which shortly after the pressing-out has started, the components present themselves at a ratio different from that at the end is not desirable. Searches of literature have shown that this separation effect which occurs when pressing out the respective substance have heretofore gone unobserved and has not been realized as an explanation of faulty results in tooth fillings. Evidently it has been held that the defects are to be attributed to an insufficient mixing of the component during the preceding mixing process. It would appear that the conclusion could be drawn that with such mixing containers, the mixing chambers or delivery tubes should be bent or curved from the very start, i.e. prior to the intermixing of the components while maintaining a substantially uniform inner cross section of the tube. However, difficulties are encountered when mixing a viscous mass in a bent tube which subsequently is to be used as delivery tube. It is for this reason that the tube should be as straight as possible during the mixing operation. The tube should furthermore not be bent during the mixing operation in a mechanical mixing device in which relatively strong forces occur.

It is, therefore, an object of the present invention with a container of the above mentioned general type, so to design the mixing chamber that on one hand during the mixing operation it will maintain its shape, and on the other hand will make possible an application of the finished mixture onto areas which are rather difficult or which are accessible under some difficulties.

These and other objects and advantages of the present invention will appear more clearly from the following specification in connection with the accompanying drawings, in which.

Figure 1:
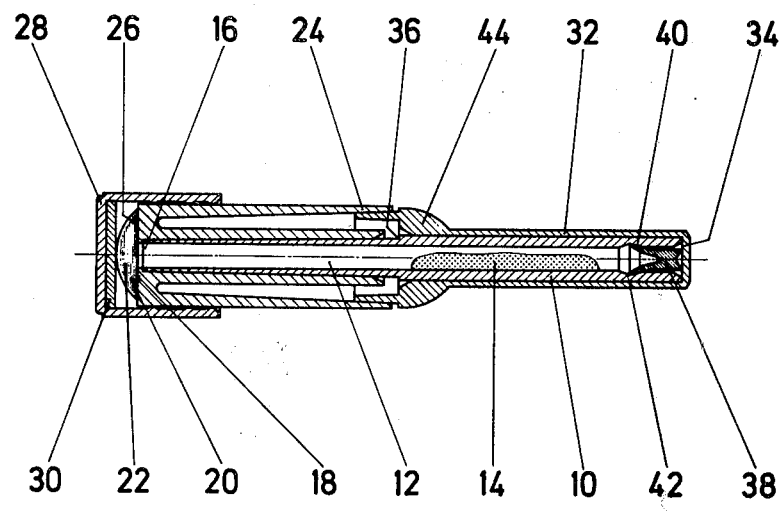
FIG. 1 illustrates a longitudinal section of an embodiment of the container according to the present invention in the form of a syringe-shaped mixing container.

As mentioned above, the present invention concerns a container for receiving substances adapted to react with each other and suitable for producing viscous medical and dental-medical preparations, especially amalgams. This container comprises a chamber for receiving a flowable substance which after elimination of a separation wall or partition is conveyed into a mixing chamber preferably containing a pulverous substance. From said mixing chamber the mixed preparation can be pressed out by means of a piston.

The container according to the present invention is characterized primarily in that the mixing chamber is at least within the region of its discharging end formed by a bendable discharging tube which is surrounded by a rigid protective sleeve or the like. By means of this container, it is possible on one hand, within a short time to obtain homogeneous viscous mixtures. On the other hand, these mixtures can be applied also easily to areas which are not easily accessible.

By means of the protective sleeve, a contamination of the surroundings by toxic mercury vapors during the mixing operation will be prevented in a reliable manner. Moreover, by simple structural steps, the protective sleeve can be so designed that the bendable delivery tube, after it has been sterilized by the manufacturer, is also totally sterile when being used by the dentist. Preferably, the bendable delivery tube is at that end thereof which is located opposite the discharge end, closed by a piston. For purposes of pressing out the finished preparation, the delivery tube is inserted in a customary delivery device, for instance a so-called amalgam dispenser, which in its simplest form as syringe-shaped instrument is provided with a curved tubular end piece.

The discharge tube is inserted into said end piece. When pressing out the finished preparation, a push rod of the delivery device presses upon the movable piston of the delivery tube. After the preparation has been discharged, the piston is at its discharge end, and the bendable tube can be eliminated together with the piston.

Preferably, the delivery tube which is bendable at least over half its length, is surrounded by a rigid protective sleeve composed of two parts. In this way, the freeing of the discharge tube at the end of the mixing operation is greatly facilitated.

According to a preferred embodiment, one part of the protective sleeve in the vicinity of the delivery end of the flexible tube is widened so as to have an abutment surface for a foil cushion which contains the flowable substance while the wall of said sleeve which rests on the supporting surface as well as the destructible partition. This portion of the protective sleeve also has a double function namely the supporting surface serves as counter pressure surface when the pressure is exerted upon the foil cushion in order to convey the flowable substance contained therein, by destruction of the partition, into the tube serving as mixing chamber.

Preferably, one portion of the protective sleeve in the vicinity of the discharging end of the bendable tube also serves as guide for actuating means for introducing the flowable substance into the bendable tube. With these actuating means, for instance a displaceable cap or a cap which can be screwed on is involved during the movement of which toward the foil cushion a pressure is exerted until the destructable partition bursts. Preferably, the inner diameter of one part of the protective sleeve is identical to the outer diameter of the bendable tube at the discharge end so that the bendable tube can be inserted tightly into said part of the protective sleeve. The bendable delivery tube preferably consists of a tube of synthetic material with smooth inner walls preferably provided with a sliding substance. As synthetic material, for instance polyethylene, polypropylene or another bendable material may be employed which as sliding substance may contain for instance a softener. The pressing out of the viscous preparation is with the container according to the invention preferably further facilitated having the substantially circular inner cross section of the bendable delivery tube gradually widened toward the delivery end. Preferably, for this purpose, the inner wall of the bendable tube has an opening angle of about from 20′ to 3°.

With this embodiment, it is expedient to provide the piston with a sealing lip in order to assure that the piston will always engage the inner walls of the bendable tube. Since, however, the sealing lips, when engaging the inner walls of the bendable tube for any length of time for instance when being stored, lose their elasticity, preferably recesses are provided on the inner side of the bendable tube which recesses are engaged by the sealing lips of the piston. It will thus be appreciated that no pressure will be exerted upon the sealing lips in its normal condition so that the sealing lips can be slightly spread outwardly and during the pressing out of the preparation will always engage the inner walls even when the bendable tube widens somewhat to its discharge end.

In order to limit the movement of the bendable tube when it is inserted into the tubular end piece of the delivery device, the outer wall of the bendable tube is preferably provided with holding projections. Expediently, these holding projections are so arranged that the inserted bendable tube projects somewhat beyond the mouth of the tubular end piece so that said end piece is not soiled by the preparation.

However, if desired, the outer diameter of the discharging tube may over its length gradually decrease toward the discharging end while the inner cross section of the tubular end piece of the discharging device likewise tapers correspondingly so that the bendable tube can easily be inserted into the end piece and can sit tight therein. The gradual taper of the outer cross section, in combination with the widening of the inner cross section at the discharging end results in a reduction of the wall thickness of the bendable tube as a result of which the flexibility of said bendable tube is increased and its introduction into the tooth cavity is facilitated.

Figure 2:
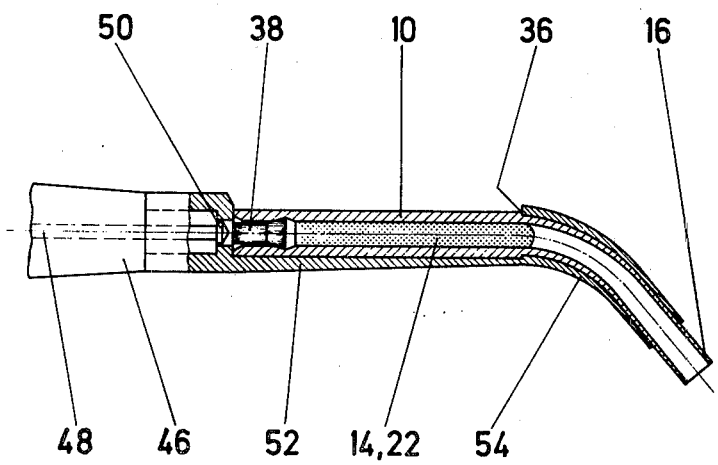
FIG. 2 illustrates a partial section through a bendable tube prior to mounting the same into the device of FIG. 1.

Referring now to the drawing in detail, FIG. 1 shows an embodiment of the invention in the form of a syringe-shaped mixing container in which the bendable tube 10 is located prior to inserting it into the pressing-out device as shown in FIG. 2. The bendable tube 10 forms the main part of the mixing container of FIG. 1 in which the mixing components are stored in separate chambers up to shortly prior to the mixing operation. The tube 10 confines the mixing chamber 12 which contains a preferably pulverous substance 14, for instance silver filings. At the discharge end 16, the bendable tube 10 is covered by the destructible partition 18 of a foil cushion 20 into which a flowable substance 22, for instance mercury, is sealed. The tube 10 is on the side of the discharge end 16 plugged into the first portion of a rigid protective sleeve composed of two parts, said first part being shown in FIG. 1 as a hollow part, but it is to be understood that it may also be a simple cylindrical tube. The part 24 in the vicinity of the discharge end 16 forms a supporting or pressure surface 26 for the destructible partition 18 of the foil cushion 20. Adjacent to the surface 26, the part 24 is designed as guiding means for a displaceable cap 28 adapted to be displaced or screwed on. This cap serves as actuating means for inserting the flowable substance 22 into the bendable tube 10. To this end, the end face of the cap 28 acts as pressure surface upon the foil cushion 20. This end face is substantially complimentary to the supporting surface 26 serving as partition for the mixing chamber 12. In order to equalize finished tolerances, for instance in order to exert a uniform pressure upon the foil cushion 20, expediently a disc 30 of elastic material such as rubber or soft synthetic material is inserted between the cap 28 and the foil cushion 20.

The second part 32 of the rigid protective sleeve surrounds the bendable tube 10 on the end 34 located opposite the discharge end, approximately up to a projection 36 which latter, as shown in FIG. 2, serves as holding projection for the tube 10. The tube 10 has thus about its half surrounded by the second part of the protective sleeve. This part of the tube does not have to be bendable under all circumstances. It will suffice when the section of the tube 10 which extends from the projection 36 to the discharge end 16 is bendable. It will be seen that the tube 10 which preferably has a circular cross section, widens toward the discharge end 16 gradually which means the wall thickness gradually decreases toward the discharge end 16, in other words the bendability increases. Customarily, the inner wall of the tube 10 has an opening angle of about 20′ to 3°.

At the end 34, the tube 10 comprises a movable piston 38 which is provided with a sealing lip 40. Said sealing lip extends into a recess 42 of the tube 10.

The second part 32 of the rigid protective sleeve is provided with a widened extension 44 which extends into the first part 24 of the rigid protective sleeve. This extension serves as counter mount when the mixing container is clamped into an oscillating mixing device.

For transferring the flowable substance 22 while destroying the partition 18 of the foil cushion 20, the cap 38 is moved in the direction of a supporting surface 26 whereby the foil cushion 20 is caused to burst. As a result thereof, the flowable substance pours into the mixing chamber 12. The mixing container is now clamped into a suitable oscillating mixing device while the fork of said device on one hand presses into the cap 28 and on the other hand presses upon the widened extension 44 of the second part 32. In this way, a separation of the mixing container during the mixing operation will be prevented.

After completion of the mixing operation, the protective sleeve of the mixing container is pulled apart by grasping the two parts 24 and 32, so that the tube 10 is first exposed on one side. Thereupon the tube 10 is grasped at the free end and is either pulled out of the part 24 or out of the part 32 of the protective sleeve.

The tube 10 which comprises the finished mixed dental preparation is now inserted into a discharging device 46 with a flexible push rod 48. On the push rod 48 there is provided a reciprocable piston 50 which contacts the piston 38. The discharging device 46 has a discharging part 52 which merges with a tubular end piece 54. This tubular end piece 54 preferably over its entire length has a practically circular cross section, and the bendable tube 10 fits while maintaining its substantially circular cross section tightly in the tubular end piece 54. In this connection, the projection 36 abuts the tubular end piece 54, and the discharge end 16 projects beyond the end of the tubular end piece 54 so that the latter is not soiled by residues of the preparation.

When actuating the push rod 48, the piston 38 is pressed steadily and the preparation designated with reference numerals 14 and 22 is through the discharge end 16 applied to the desired area without the separation to be feared, especially with amalgams, between pulverous and flowable components being encountered.

It will be seen that the bendable tube 10 can be inserted into tubular end pieces 54 at different curvature so that for all cases of application only one type of bendable tube has to be employed whereby it is also possible to get by with one type of mixing container according to FIG. 1.

It is, of course, to be understood that the present invention is, by no means, limited to the specific showing in the drawing, but also comprises any modifications within the scope of the appended claims.

Thus, the curved, rigid walled tubular end piece 54 need not be fixedly connected to the discharge part 52 of the discharging device 46 but it may for instance also be screwed on whereby it will be possible to employ end pieces 54 with a single discharge device 56, while each end piece 54 may be curved to a different extent.

What is claimed is:

1. A container construction for receiving substances adapted to combine with each other for producing viscous medical and dental preparations, especially amalgams, which comprises in combination: chamber means receiving a flowable substance to form a first component of the preparation to be produced, a mixing chamber formed by a flexible member receiving at least a second component of the preparation to be produced, said chamber means being positioned to convey flowable substance therein to said mixing chamber, means for bringing about intermixing with the content of the latter, said mixing chamber having a discharge end and at least within the region of said discharge end comprising a flexible discharge tubular section projecting therefrom as well as bendable angularly for application of the preparation mixed in the container for distribution into differing dental-medical locations and a rigid protective sleeve surrounding said flexible discharge tubular section and being detachable relative thereto.

2. A container construction in combination according to claim 1, in which said mixing chamber opposite its discharge end has a piston displaceably arranged therein.

3. A container construction in combination according to claim 1, in which said flexible discharge tubular section forms at least half of a discharge tube, and in which said rigid protective sleeve comprises a first section adjacent said chamber means and a second section adjacent said first section and extending over at least the major portion of the remaining extension of said mixing chamber.

4. A container construction in combination according to claim 3, in which said first section of said protective sleeve is closed relative to said chamber means by a destructable wall section.

5. A container construction in combination according to claim 1, in which said chamber means includes a foil cushion containing a flowable substance and comprising a destructable wall section.

6. A container construction in combination according to claim 5, in which said first section of said protective sleeve is in the vicinity of said discharge end widened to form a supporting surface for a portion of said destructable wall section of said foil cushion.

7. A container construction in combination according to claim 5, which includes actuating means guided on said protective sleeve and operable to break said destructable wall section and to transfer flowable substance from said foil cushion to said mixing chamber.

8. A container construction in combination according to claim 1, in which the inner diameter of said protective sleeve fits substantially with slide fit on the outer surface of said flexible discharge tubular section.

9. A container construction in combination according to claim 1, in which said flexible tubular section is a tube of synthetic material having smooth inner walls.

10. A container construction in combination according to claim 9, in which the inner wall of said tube is provided with a sliding substance.

11. A container construction in combination according to claim 1, in which the inner cross section of said flexible tube section is circular and gradually widens in the direction toward said discharging end.

12. A container construction in combination according to claim 11, in which said flexible tube section has an opening angle of from about 20' to 3°.

13. A container construction in combination according to claim 2, in which said tubular section is provided with recess means, and also is provided with a sealing lip engaging said recess means.

14. A container construction in combination according to claim 1, in which the outer wall of said flexible tubular section is provided with holding projections.

15. A container construction in combination according to claim 3, in which said second section of said rigid protective sleeve has that end which abuts said first section of said rigid protective sleeve provided with an outer flange portion.

16. A container construction in combination according to claim 1, in which the outer diameter of said flexible discharge tubular section gradually decreases over its length.

17. A container construction in combination according to claim 1, in which the wall thickness of said flexible discharge tubular section decreases in the direction toward the discharge end thereof.

* * * * *